United States Patent [19]

Durr et al.

[11] Patent Number: 4,844,612

[45] Date of Patent: Jul. 4, 1989

[54] APPARATUS FOR THE ANALYSIS OF ELEMENTS BY INDUCTIVE PLASMA SPECTROMETRY PRODUCED BY AIR

[75] Inventors: René C. Durr, Albertville; Jean-Pierre Rozain, Fontaine Les Dijon, both of France

[73] Assignee: Commissariat a L'Energie Atomique, Paris, France

[21] Appl. No.: 103,888

[22] Filed: Oct. 2, 1987

[30] Foreign Application Priority Data

Oct. 3, 1986 [FR] France ................... 86 13837

[51] Int. Cl.[4] .................. G01J 3/443; G01N 21/73
[52] U.S. Cl. ..................................... 356/316
[58] Field of Search ......... 356/316; 219/121, 121 PQ, 219/121 PT, 121 PU, 121 PW

[56] References Cited

U.S. PATENT DOCUMENTS 3,958,883 5/1976 Turner ......................... 356/316
4,311,897 1/1982 Yerushalmy ............. 219/121 PQ
4,482,246 11/1984 Meyer et al. ................... 356/316

FOREIGN PATENT DOCUMENTS 58-87446 5/1983 Japan.
1109602 4/1968 United Kingdom ............... 356/316

OTHER PUBLICATIONS

Applied Spectroscopy 39, (2), 226–230, (1985), Y. K. Zhang et al., "Evaluation of Microwave—Induced Air—Plasma . . . ".
Applied Spectroscopy 37, (2), 101–105, (1983), J. P. Keilsohn et al., "The Use of a Microarc Atomizer . . . ".

Primary Examiner—F. L. Evans
Attorney, Agent, or Firm—Michael N. Meller

[57] ABSTRACT

Apparatus for analysing elements by inductive plasma spectrometry produced by the air. It comprises a tube, means for producing within said tube a plasma containing the element and means for the spectrometric analysis of the like from the plasma. The plasma production means incorporate means for circulating air in the tube, said air serving to produce the plasma. Application to the analysis of an element contained in the air.

10 Claims, 3 Drawing Sheets

APPARATUS FOR THE ANALYSIS OF ELEMENTS BY INDUCTIVE PLASMA SPECTROMETRY PRODUCED BY AIR

BACKGROUND OF THE INVENTION

The present invention relates to an apparatus for the analysis of elements by inductive plasma spectrometry produced by air. It more particularly applies to the analysis of elements, such as beryllium, which may be contained in air and more generally to the analysis of elements likely to be present in aerosols, liquids, or gases.

"analysis" is understood to means a detection possibly accompanied by dosing and the element can be a solid (e.g. solid particles contained in air), a liquid or a gas (e.g. carbon dioxide gas in the air).

An apparatus for the analysis of elements by plasma spectrometry is already known. This apparatus, which is diagrammatically shown in FIG. 1, comprises a tube 2 made from a refractory material, an exciting source, constituted by an induction coil 4 surrounding a central portion of the tube and energized by a high frequency generator 6, a double injection system 8 permitting the injection of argon as the plasmagenic gas, as well as the central injection of a liquid solution (or vapours of a solution) containing the element to be analysed and a spectrophotometer 10 permitting the analysis of the light emitted by the plasma formed in the tube, in the central portion thereof, and the measurement of the intensity of a characteristic emission line of the element to be analysed, said measurement representing the concentration of said element in the solution.

The light emitted by the plasma is collected by a lens 12, which focuses said light onto the entrance of the spectrophotometer and the latter is connected to a measuring means such as a galvanometer 14, which makes it possible to measure said intensity.

The tube 2 is open at one end and closed at its other end. As can be seen in FIG. 2, an intermediate tube 16, coaxial to tube 2, extends within the latter between said closed end and coil 4. The intermediate tube 16, whose diameter is obviously smaller than that of tube 2, has an open end and another closed end coinciding with the closed end of tube 2.

An injection tube 18, whose diameter is smaller than that of the intermediate tube 16 traverses, parallel to the axis of tube 2 and in a tight manner, the closed end of intermediate tube 16 and ends substantially level with the open end of tube 16.

The injection means 8 compromise a compressed argon cylinder 20, which communicates in tight manner, via a valve 23 and in the vicinity of the closed end of tube 2, with the space between said tube 2 and the intermediate tube 16.

With a view to the injection of the solution, the injection means 8 also comprise injection tube 18, a chamber 22 connected to the end of tube 18, which is not located within tube 2, an atomizer 24 controlled by a not shown ultrasonic generator and communicating with said chamber 22, said atomizer serving to contain the solution to be injected, a compressed argon cylinder 26 communicating on the one hand with the atomizer 24 and on the other with the chamber 22, by means of a member 28 making it possible to pass argon from cylinder 26 to chamber 22 and to atomizer 24.

When the ultrasonic generator is operating and the argon from cylinder 26 reaches chamber 22, small droplets of solution, formed by the ultrasonics in the atomizer 24 and which reach the chamber 22, are entrained by the argon into injection tube 18.

A plasma 30 containing the element to be analysed is then formed, as a result of the argon coming from cylinder 20, in that portion of tube 2 surrounded by the turns of coil 4. The light emitted by the plasma is analysed by the spectrophotometer 10.

Thus, the operation of the known apparatus, diagrammatically shown in FIG. 1, requires the injection of argon as the plasmagenic gas for forming and maintaining the plasma, as well as the injection of the solution to be analysed into the central channel of the plasma torch, said central channel being the injection tube 8 and the torch comprising the tubes 2, 16 and 18.

The apparatus shown in FIG. 1 suffers from the disadvantage of not permitting the direct analysis of an element, such as beryllium, liable to be contained in air. Thus, for analysing the beryllium contained in air, it is firstly necessary to trap said beryllium on a filter and produce a solution from the beryllium trapped on the filter, so that the analysis of the beryllium is carried out a posteriori through the apparatus shown in FIG. 1.

SUMMARY OF THE INVENTION

The present invention relates to an apparatus for the analysis of an element, said apparatus comprising in per se known manner means for creating in a tube a plasma containing the element, said creation means incorporating means for inducing an electromagnetic field in a portion of the tube. This apparatus obviates the disadvantage referred to hereinbefore whilst increasing, compared with the known apparatuses, the presence time of the element to be analysed in said portion of the tube and therefore the sensitivity of the apparatus.

More specifically, the present invention relates to an apparatus for the analysis of an element, said apparatus comprising a tube, means for producing in said tube a plasma containing the element, said production means having means for inducing an electromagnetic field in a portion of said tube and means for circulating air within said tube, said air serving to produce the plasma without any initial supply of any other plasmagenic gas, and means for the spectrometric analysis of the light from the plasma, wherein the air circulation means comprise means for the entry of air at one end of the tube, said air entry means have a part along which circulates the air and which extends in the tube from said one end of said tube to the vicinity of said position of said tube, the cross-section of said part considered transversely to the axis of the tube is small compared with that of said tube, at least on the side of said position of said tube, so as to slow down the flow of air into a zone which extends along the axis of said tube, which is of small size considered transversely to said axis and which is located in said portion of said tube.

The term "small cross-section compared with that of said tube" is understood to means cross-section of said part not exceeding approximately 20% and preferably 5% of the cross-section of said tube.

Due to the fact that apparatus according to the invention uses air as the plasmagenic gas, said apparatus permits the direct analysis of an element, e.g. beryllium, liable to be contained in the air.

Thus, the apparatus according to the invention can function solely with air, without the addition of any other plasmagenic gas, even during the ignition of the plasma. Moreover, the present invention makes it possible to obviate the need for injecting a solution containing an element to be analysed into the central channel of a plasma torch.

Thus, it is possible to simplify the analysis of an element and it is possible to analyse a pollutant of the air with a large sampled air quantity. Moreover, due to the small cross-section of said part, at least on the side of said portion of said tube, it is possible to facilitate the ignition and maintaining in form of the plasma and in particular it is possible to extend the presence time of the element to be analysed in said portion, which makes it possible to excite a sufficient quantity of said element with a view to the analysis thereof.

In a first special embodiment, the air entry means also comprise means for supplying said air part and said tube, on the side of said one end of said tube, wherein said cross-section of said part considered transversely to said tube axis is smaller on the side of said portion of said tube than at said one end of said tube.

In a second embodiment, the tube is open at said one end thereof, wherein said part has an end located outside said tube, on the side of said one end of said tube, and extends into said tube into the vicinity of said portion of said tube, the end of said part located outside said tube being profiled.

In this second embodiment, the air entry means can also comprise blades or fins which connect said part to said tube and which are provided to bring about a helical of the air flow.

Preferably, the air circulation means comprise means for the suction of air at the other end of the tube. In the case where the element to be analysed is in the form of a aerosol, the apparatus according to the invention also has means for sampling said aerosol, such a vacuum operation (the means for ensuring the air flow being located downstream of the plasma torch, i.e. of the tube part where the plasma is formed) makes it possible to minimize the retention of particles of the aerosol in said sampling means.

If the retention problem is considered to be insignificant, the means for ensuring the air flow can be positioned upstream of the plasma torch. The air entry means can then have means for forcing the air into the tube.

According to another embodiment of the apparatus according to the invention, the means for producing the plasma comprise means for igniting said plasma, which have a rod parallel to the axis of the tube and which is mobile with respect to said axis. Such plasma production means are particularly suitable for the two embodiments described hereinbefore.

In another embodiment of the invention, the plasma ignition means could comprise for producing a spark in said portion of the tube (in which the electromagnetic field is induced).

Finally, according to another embodiment of the apparatus according to the invention, the means for producing the plasma also comprise means for injecting into the tube and along the axis thereof a gas carrying droplets containing the element to be analysed.

In this case, the apparatus according to the invention not only makes it possible to analyse an element likely to be contained in the air, but also an element contained in a liquid solution.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
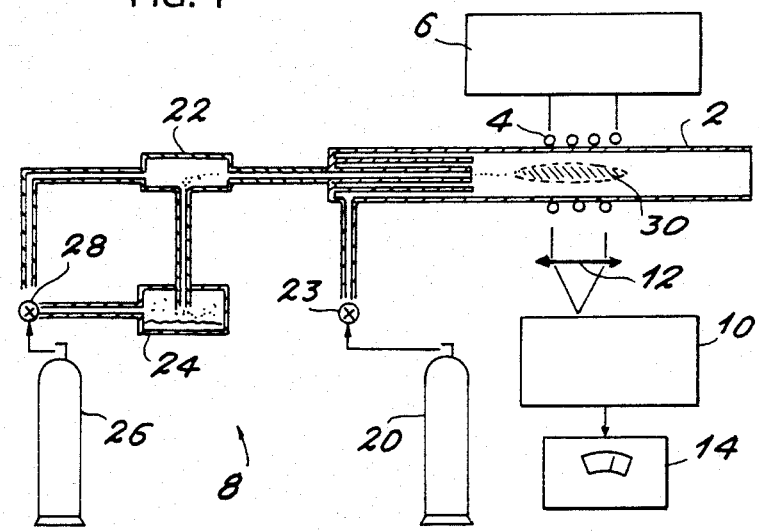
FIG. 1, a diagrammatic view of an apparatus for analysing elements by inductive plasma spectrometry, which is known in the art and which has already been described.
Figure 2:
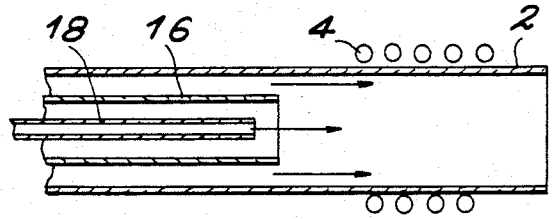
FIG. 2, a view of part of the apparatus shown in FIG. 1 and which has already been described.
Figure 3:
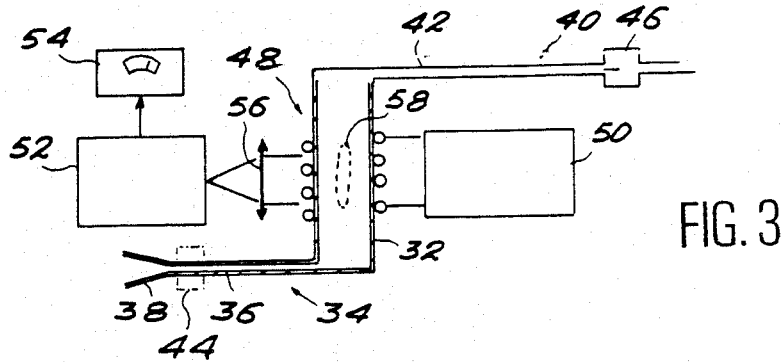
FIG. 3, a diagrammatic view of an embodiment of the apparatus according to the invention.

FIG. 3 diagrammatically shows a special embodiment of the apparatus according to the invention. The apparatus then comprises:

an external tube 32 made from a refractory material, such as silica or alumina;

means 34 from the entry of air into tube 32, said air entry means having means for supplying air, for example, a silica tube 36, whereof one end is sealingly connected, in the manner shown hereinafter (FIGS. 5 and 6) to one end of tube 32, whilst the other end of tube 36 is provided with an air sampling cone 38;

means 40 for the circulating the air contained in tube 32, said means 40 having e.g. a silicon tube 42 sealingly connected by one end to the other end of tube 32, the outflow of air from tube 32 e.g. taking place tangentially (after cooling by passing, if necessary, through a not shown refrigerator), the means 40 also having a pump 46 for the suction of air at the other end of tube 42;

a coil 48, whose turns surround a central portion of tube 32 and which is energized by a high frequency generator 50; a spectrophotometer 52 provided with measurement display means and e.g. constituted by a galvanometer 54; and a lens 56 for focusing the light produced by a plasma likely to be formed in tube 32 on an intake diaphragm of the spectrophotometer 52.

Coil 48, associated with generator 50, has the function of producing and maintaining the plasma produced by the air circulating in tube 32. The opening or aperture angle of the sampling cone 38 can be calculated as a function of the diameter of the particles likely to be detected by the apparatus according to the invention, so as to minimize the retention of these particles in the cone 38.

When the pump 46 operates, the air sucked in by cone 38 circulates in tube 32. The operation of generator 50 then permits the creation of a plasma 58 in tube 32, in the portion thereof surrounded by the turns of coil 48.

The light emitted by the plasma is then detected by the spectrophotometer 52.

When operating in "emission", an element present in the sucked air contributes to the formation of the plasma and a light characteristic of said element is then transmitted by said plasma and analysed by the spectrophotometer.

Figure 4:
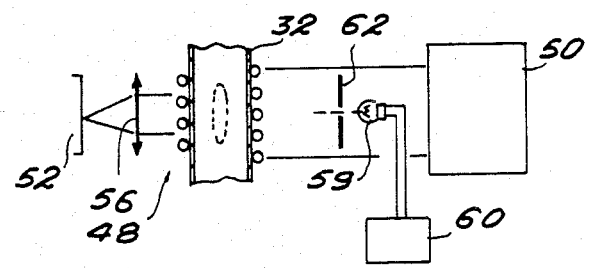
FIG. 4, a partial, diagrammatic view of a variant of the apparatus shown in FIG. 3.

In a construction variant (FIG. 4), measurements are carried out in "absorption" and to the apparatus shown in FIG. 3 is then added a lamp 59 containing an element identical to that assumed to be contained in the air and which it is wished to analyse e.g. a lamp, whose filament contains beryllium, if it is wished to analyse the beryllium contained in the air), said lamp being supplied by a power supply 60. The apparatus is also equipped with a diaphragm 62 located between lamp 59 and tube 32. The lamp 59, the opening of its diaphragm 62 and the opening of the spectrophotometer diaphragm are aligned in accordance with a diameter of the tube 32, the lamp being opposite to lens 56 with respect to said tube 32 and the turns of coil 48 are sufficiently spaced to permit the passage of the diaphragmed light from lamp 59.

With regards to the circulation of air in tube 32 (FIG. 3), pump 46 could be illuminated (tube 42 then being open at its other end) and following cone 38 is then mounted on tube 36 a fan 44 for forcing the air into tube 32. However, this construction (use of a fan) is only if interest for analysing gases or possibly liquids. The following cone 38 and the tube 36 can be in general terms refer to as "means for supplying air".

Figure 5:
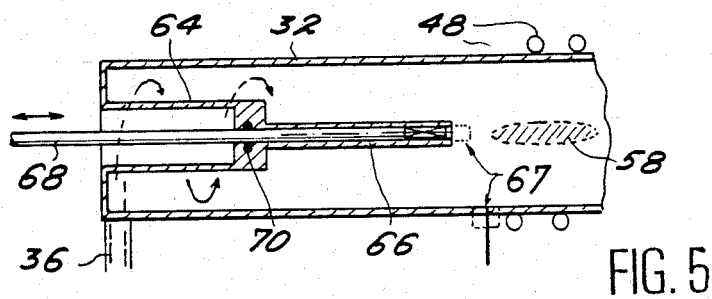
FIG. 5, a diagrammatic view of a first embodiment of an air intake forming part of the apparatus shown in FIG. 3.

FIG. 5 diagrammatically shows a first construction of means 34, which permits a tangential entry of air into tube 32. In this first embodiment, the apparatus comprises a part consisting of a hollow or solid cylinder 64, and another solid or hollow cylinder 66. the hollow or solid cylinder 64, e.g. of silica and having a preferably slightly smaller diameter to the internal diameter of tube 32 is mounted within said tube 32 and coaxial thereto. One end cylinder 64 is connected to end of tube 32, on the side of which where entry of air takes place.

Another solid or hollow cylinder 66, e.g. of silica, having a diameter smaller than that o cylinder 64 (cf FIG. 5) extends into tube 32 along the axis of the latter, between the other end of cylinder 64 and that portion of tube 32 surrounded by coil 48, one end of cylinder 66 being welded to the other end of cylinder 64. Preferably, the diameter of cylinder 66 is less than approximately 0.2 times the internal diameter of tube 32.

Said end of tube 36 is connected tangentially by welding to tube 32 and communicates with the space between said tube 32 and cylinder 64 on the side of the end of tube 32.

The assembly formed by tube 32 and cylinder 64, 66 is designed in such a way that the air does not escape to the outside of tube 32 when it reenters there. For example, when cylinder 64 is hollow, its ends are respectively sealingly connected, e.g. by welding, to said ends of tube 32 and cylinder 66, no matter whether the latter is hollow or solid, the other end of cylinder 66 being closed when the latter is hollow.

When cylinder 64 is solid, said end of this cylinder is sealingly connected to the end of tube 32 and the other end of cylinder 64 is fixed to cylinder 66, no matter whether it is solid or hollow. It is also possible to produce a tube 32 sealed at said end and to respectively fix the ends of cylinder 64 to said closed end and to said end of cylinder 66.

The air, which enters tube 32 tangentially, has a helical trajectory along cylinder 64 and, according to the laws of the mechanics of fluids, cylinder 66, whose diameter is smaller than that of cylinder 64, makes it possible to slow down the central part of the air flow and consequently obtain a long presence time of the element contained in the air (e.g. in the form of solid particles, such as beryllium particles) in the central portion of tube 32, which makes it possible to excite an adequate quantity of the element in order to analyse the same.

The ignition of the plasma can be obtained by means of a rod 68, e.g. of graphite, alumina or tungsten, which traverses cylinders 64, 66 parallel to the axis of tube 32 and which can be moved parallel to said axis from the exterior of tube 32. A gasket 70 is provided at the location of cylinder 64 where rod 68 penetrates (located on the side of the air intake), in the case where cylinder 64 is solid. When cylinder 64 is hollow, gasket 70 can be placed level with the tight connection between cylinders 64 and 66. When tube 32 is closed at said end thereof, the gasket can be placed at said end.

The ignition of the plasma is obtained on moving out of cylinder 66 the end of rod 68 located therein and which can have a swelling, in order to place said end in the portion surrounded by coil 48, rod 86 being retracted when the plasma is ignited.

In a constructional variant, it would be possible to use for the ignition of the plasma, a means 67 for producing sparks in the portion tube 32 in which the electromagnetic field is induced.

Figure 6:
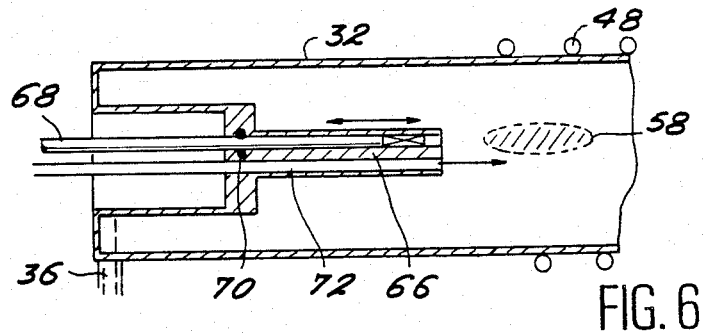
FIG. 6, a diagrammatic view of a variant of the air intake shown in FIG. 5 also permitting the injection of aerosols into the apparatus shown in FIG. 3.

FIG. 6 diagrammatically shows a construction variant of the apparatus shown in FIG. 5 not only permitting the analysis of air, but also the analysis of an aerosol from a liquid solution. In the apparatus of FIG. 6, cylinders 64 and 66 are not only traversed by the rod 68 parallel to the axis of tube 32, but also by an aerosol injection tube 72 parallel to the axis of tube 32, the passage of said tube 72 being tight as a result of a not shown gasket or a tight welding of a portion of the periphery of tube 72 e.g. to cylinder 66.

Figure 7:
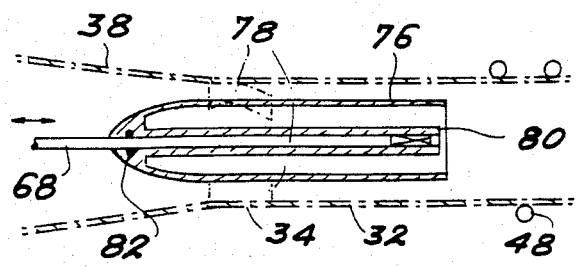
FIG. 7, a diagrammatic view of a second embodiment of the air intake.

FIG. 7 diagrammatically shows a second embodiment of means 34 permitting the entry of air into the apparatus parallel to the axis of tube 32.

In this embodiment, the end of tube 32, where air entry takes place, is open and the sampling cone 38 is directly connected to said end of tube 32.

The apparatus shown in FIG. 7 also comprises a central part 76, e.g. of silica. One end of part 76 is located in sampling cone 38. The other end of part 76 is located in the vicinity of the end coil 48 facing sampling cone 38. part 76 extends parallel to the axis of tube 32 and is also fixed thereto.

Figure 8:
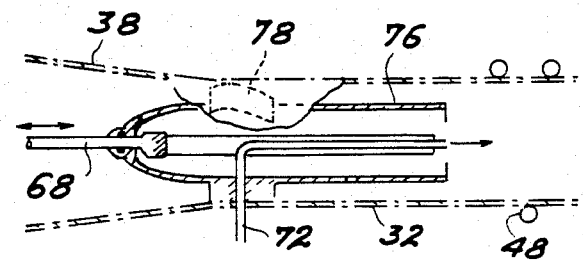
FIG. 8, a diagrammatic view of a variant of the air intake shown in FIG. 7 also permitting the injection of aerosols into the apparatus shown in FIG. 3.

The end of part 76 located in sampling cone 38 is profiled (e.g. being shaped like an ogive), so as to minimize the retention of particles likely to be contained in the air within the sampling cone 38. In its non-profiled portion, part 76 adapts to the shape of a cylinder revolution, whose diameter is less than approximately 0.2 times the internal diameter of tube 32 and which is shown in exaggerated form in FIG. 7 (and in FIG. 8) for reasons of clarity. The particles contained in the air are greatly slowed down when they reach the portion of tube 32 surrounded by the coil turns.

Part 76 can be fixed to tube 32 via small ribs 78 connecting a portion of the periphery of the part 76 located in the vicinity of the junction between the sampling cone and the tube 32. These fins can have a shape able to give a helical movement to the entering air flow. The e.g. silica part 76 can be solid or hollow.

A rod 68 for igniting the plasma can be provided in the apparatus shown in FIG. 7. Rod 68 can be displaced, from the out side of the apparatus, parallel to the axis of tube 32 and traverses part 76. When the latter is solid, a duct can be provided for passing through rod 68. When part 76 is hollow, for said passage it is e.g. possible to provide an e.g. silica inner tube 80 having a diameter appropriate for the displacement of rod 86 (and smaller than the diameter of the cylindrical portion of part 76), tube 80 being welded to the profiled end of part 76. A gasket 82 is provided at the point where rod 68 enters part 76 by the profiled portion of the latter.

In a construction variant permitting the injection of an aerosol coming from a solution into the apparatus (fig 8), an aerosol injection tube 72 sealingly traverses tube 32 (through welding the periphery of tube 72 to tube 32 at the point where tube 72 enters the latter), the passage e.g. taking place level with fins 72. Tube 72 penetrates tube 32 perpendicular to the axis of the latter and then bends so as to follow axis 32 and stops substantially level with end of part 76 located in tube 32.

The ignition rod 68 can also be used in the apparatus of FIG. 8. For this purpose, part 76 is e.g. hollow and the portion of rod 68 located in part 76 is hollow and longitudinally slotted in such a way that the slotted portion can move, whilst bearing on the portion of tube 72 extending along the axis of tube 32.

As a variant, part 76 could be solid (tube 72 still traversing it and issuing at the end of part 76 located in tube 32) and rod 68 would slide in part 76 parallel to the axis of tube 32, but not in accordance with the axis thereof.

Moreover, rod 68 (FIG. 6 and 8) could be replaced by other known plasma ignition means. Furthermore, the end of tube 72 (FIG. 6 and 8), located outside tube 32, could be connected to an aerosol injection system of the type comprising members 22 to 28 of FIG. 1.

Obviously, for special constructions having rod 68 and/or tube 72, the diameters of parts 64, 66, 76 and 80 would be chosen as a function thereof.

What is claimed is:

1. An apparatus for the analysis of an element, said apparatus comprising:

a tube;

means for producing in said tube a plasma containing the element, said plasma production means having means for inducing an electromagnetic field in a portion of said tube and means for circulating air within said tube, said air serving to produce the plasma without any initial supply of any other plasmagenic gas, and means for the spectrometric analysis of the light from the plasma;

wherein said air circulation means comprising means for the entry of air at one end of said tube, said air entry means having a part along which circulates the air, which extends in said tube from said one end of said tube to the vicinity of said portion of said tube, the cross-section of said part considered transversely to the axis of said tube is small compared with that of said tube, at least on the side of said portion of said tube, so as to slow down the flow of air into a zone which extends along the axis of said tube, which is of small size considered transversely to said axis and which is located in said portion of said tube.

2. An apparatus according to claim 1, wherein said air entry means further comprising means for supplying air between said part and said tube, on the side of said one end of said tube, the cross-section of said part considered transversely to the axis of said tube is smaller on the side of said portion than at said one end of said tube.

3. An apparatus according to claim 1, wherein said tube is open at said one end thereof, said part having an end located outside said tube, on the side of said one end of said tube, and extending into said tube up to the vicinity of said portion of said tube, the end of said part located outside said tube being profiled.

4. An apparatus according to claim 3, wherein said air entry means further having fins which connect said part to said tube and which bring about a helical flow of the air.

5. An apparatus according to claim 1, wherein said air circulation means further comprising means for the suction of air at the other end of said tube.

6. An apparatus according to claim 5, wherein in the case where the element to be analyzed is in the form of an aerosol, the apparatus further comprising means for sampling said aerosol.

7. An apparatus according to claim 1, wherein said air entry means are equipped with means for forcing the air into said tube.

8. An apparatus according to claim 2, wherein said plasma production means further comprising means for igniting said plasma, said ignition means having a rod parallel to the axis of said tube and mobile parallel to axis.

9. An apparatus according to claim 2, wherein said plasma production means further comprising means for igniting said plasma, said ignition means having means for producing a spark in said portion of said tube.

10. An apparatus according to claim 1, wherein said plasma production means further comprising means for the injection into the tube along the axis thereof a gas carrying droplets containing the element to be analyzed.

* * * * *